US007819336B2

(12) United States Patent
Newman

(10) Patent No.: US 7,819,336 B2
(45) Date of Patent: Oct. 26, 2010

(54) MULTI-LAYER FRAGRANCE DELIVERY SYSTEM

(75) Inventor: Ron Newman, Murrieta, CA (US)

(73) Assignee: Latitudes International, Rancho Dominguez, CA (US)

(*) Notice: Subject to any disclaimer, the term of this patent is extended or adjusted under 35 U.S.C. 154(b) by 305 days.

(21) Appl. No.: 11/876,113

(22) Filed: Oct. 22, 2007

(65) Prior Publication Data

US 2009/0101729 A1    Apr. 23, 2009

(51) Int. Cl.
*A24F 25/00* (2006.01)
(52) U.S. Cl. .......................... 239/44; 239/34; 239/145; 422/120; 424/76.2; 512/1
(58) Field of Classification Search ............... 239/34, 239/44, 45, 49, 145; 422/123, 120; 424/76.2; 512/1–3; 392/395
See application file for complete search history.

(56) References Cited

U.S. PATENT DOCUMENTS

| 4,323,193 | A | * | 4/1982 | Compton et al. .............. 239/44 |
| 5,840,257 | A | | 11/1998 | Bureau et al. |
| 6,104,867 | A | * | 8/2000 | Stathakis et al. ............ 392/395 |
| 6,871,794 | B2 | * | 3/2005 | McEwen ...................... 239/44 |
| 6,899,280 | B2 | | 5/2005 | Kotary et al. |
| 7,055,764 | B1 | * | 6/2006 | Martinez et al. ............ 239/145 |
| 2004/0262418 | A1 | | 12/2004 | Smith et al. |
| 2008/0308648 | A1 | * | 12/2008 | Pesu ........................... 239/44 |

FOREIGN PATENT DOCUMENTS

WO    2006086904 A1    8/2006

\* cited by examiner

*Primary Examiner*—Steven J Ganey
(74) *Attorney, Agent, or Firm*—Fulwider Patton LLP

(57) ABSTRACT

A fragrance is held in one or more layers of a three-layer liquid mixture. The three layers are mutually immiscible to form an aesthetically pleasing effect while the specific gravities of the layers are adjusted so as to provide for their transfer to the atmosphere via a simple wick. Such adjustment is determined as a function of the wicking material that is used. The formulation of the mixture involves the combination of two mutually immiscible non-aqueous components that are temporarily rendered miscible during the formulation process.

14 Claims, 1 Drawing Sheet

MULTI-LAYER FRAGRANCE DELIVERY SYSTEM

This invention generally relates to a fragrance delivery system and the formulation thereof. The system is formulated so as to be displayable in an aesthetically pleasing form and for gradual release into the atmosphere. More particularly, the invention pertains to a layered combination of immiscible fragrance-bearing liquids that are simultaneously deliverable through a simple wick configuration.

BACKGROUND OF THE INVENTION

A variety of fragrance delivery systems are known including systems which provide for the wicking of a liquid containing a fragrance into the atmosphere. Wick systems have also been previously employed to simultaneously deliver two liquids wherein the liquids are either contained in separate containers or the liquids are immiscible and form distinct layers in a single container. Two such liquids may be relied upon to each carry a different fragrance or fragrance components. Such systems have also been relied upon to deliver a fragrance with a biocide or insecticide or a fragrance with an odor neutralizer or any other combination of volatile substances with or without active ingredients.

The two liquids may be selected so as to for example support an aqueous based component in combination with for example an organic solvent based component. By combining two immiscible liquids in a single transparent container, the appearance of the resulting formation of two distinct layers can be exploited for its decorative effect. Relying on a wicking system to deliver the components of two layers into the atmosphere has previously been accomplished by using either multiple wicks or a compound wick wherein separated wicking paths are provided in a single wick element. Such configurations increase the complexity and cost of fragrance delivery systems.

A delivery system is needed which allows for a plurality of immiscible liquids to be simultaneously delivered through a simple wick. Additionally, it is most desirable to be able to reduce the number of steps in the formulation process of compositions that yield multiple layers of immiscible liquids.

SUMMARY OF THE INVENTION

The present invention provides a fragrance delivery system by which multiple immiscible liquids are deliverable to the atmosphere through a simple wick. The fragrance or fragrance components are supported by one or more of the liquids while at least three layers form to provide an especially pleasing decorative effect. The appearance of the discrete layers may further be enhanced by imparting different colors or hues to each.

The present invention is directed to the arrangement of the liquid layers as a function of the wicking material that is to be used wherein such wicking material is configured to provide a common wicking path for all of the liquids. Such wick configuration is referred to herein as a "simple wick" so as to be distinguished from a wick having a compound or complex structure that simultaneously avails different wicking paths for different liquids. More specifically, it has unexpectedly been found that the use of a non-polar wicking material requires a different arrangement of the liquid layers than does the use of a polar wicking material in order to maximize the wicking action. In the event a non-polar wicking material is to be used, it has been found to be desirable to arrange the liquids such that the liquid with the highest vapor pressure comprises the top layer and the liquid with the lowest vapor pressure comprises the bottom layer. If on the other hand a polar wicking material is to be used, it has been found to be desirable to arrange the liquids such that the liquid with greatest polarity comprises the bottom layer while the liquid with the lowest polarity comprises the top layer. Thus, in accordance with the present invention, the specific gravities of one or more of the liquids is adjusted so as to achieve the desired sequence of layers. The resulting arrangement of layers has unexpectedly been found to allow for the use of a simple wick whereby an orderly and unobstructed migration of liquids through the wick and subsequent evaporation therefrom is achieved despite the liquids' mutual immiscibilities.

A variety of different liquids may be employed in accordance with the invention. A preferred combination may for example include a highly polar solvent, a volatile silicone and an aryl alcohol. Depending upon the typing of wicking material that is to be used, adjustment of the specific gravity of one or more of the liquids may be necessary in order to achieve the desired sequence that is either tied to the polar nature or the vapor pressure of each of the liquids. This is achieved by for example adding selectively miscible liquids, salts or other materials to one or more of the liquids. Additionally, materials may be added to all or to selected liquids for the purpose of pH adjustment, stabilization, metal ion sequestration, promotion of liquid separation, inhibition of microbial growth, prevention of oxidation, and for imparting or changing the color of one or more liquids including dyes and UV absorbers, etc, all while maintaining the desired relative specific gravities.

The present invention also provides for a method of combining these materials so as to streamline and expedite the formulation process. Accordingly, a three layer system is formulated by combining all of the non-aqueous components with one another prior to combining such mixture with the pre-mixed aqueous components in order to obviate the need to first premix each of the different non-aqueous components separately. A controlling solvent is used to render all of the non-aqueous components temporarily miscible. After combining all of the components, a gradual separation of the aqueous layer as well as the non-aqueous layers will occur as contact with the aqueous components will counteract the controlling solvent's effect.

The fragrance that is added to the formulation will typically become partitioned amongst the three layers. Generally defined, the fragrance comprises a substance or complex mixture of aroma chemicals, natural essential oils and other functional products, the sole purpose of which is to impart an odor or scent, or to counteract a malodor.

An appropriate wicking material has a capillary or porous structure that avails a wicking path from below the level of the densest of the liquids to above the level of the liquids where evaporation can take place. A minimum porosity (void fraction) of 0.3 and a mean pore diameter of less than 250 um, with adequate surface area exposed above the top of the liquid-containing vessel have been found to achieve satisfactory results for the delivery system of the present invention. Rattan core, sometimes referred to as reed is an example of a polar wicking material while non-woven fiberglass is an example of a non-polar wicking material.

These and other advantages of the present invention will become apparent from the following detailed description of preferred embodiments which, taken in conjunction with the drawings, illustrate by way of example the principles of the invention.

DETAILED DESCRIPTION OF THE PREFERRED EMBODIMENTS

Figure 1:
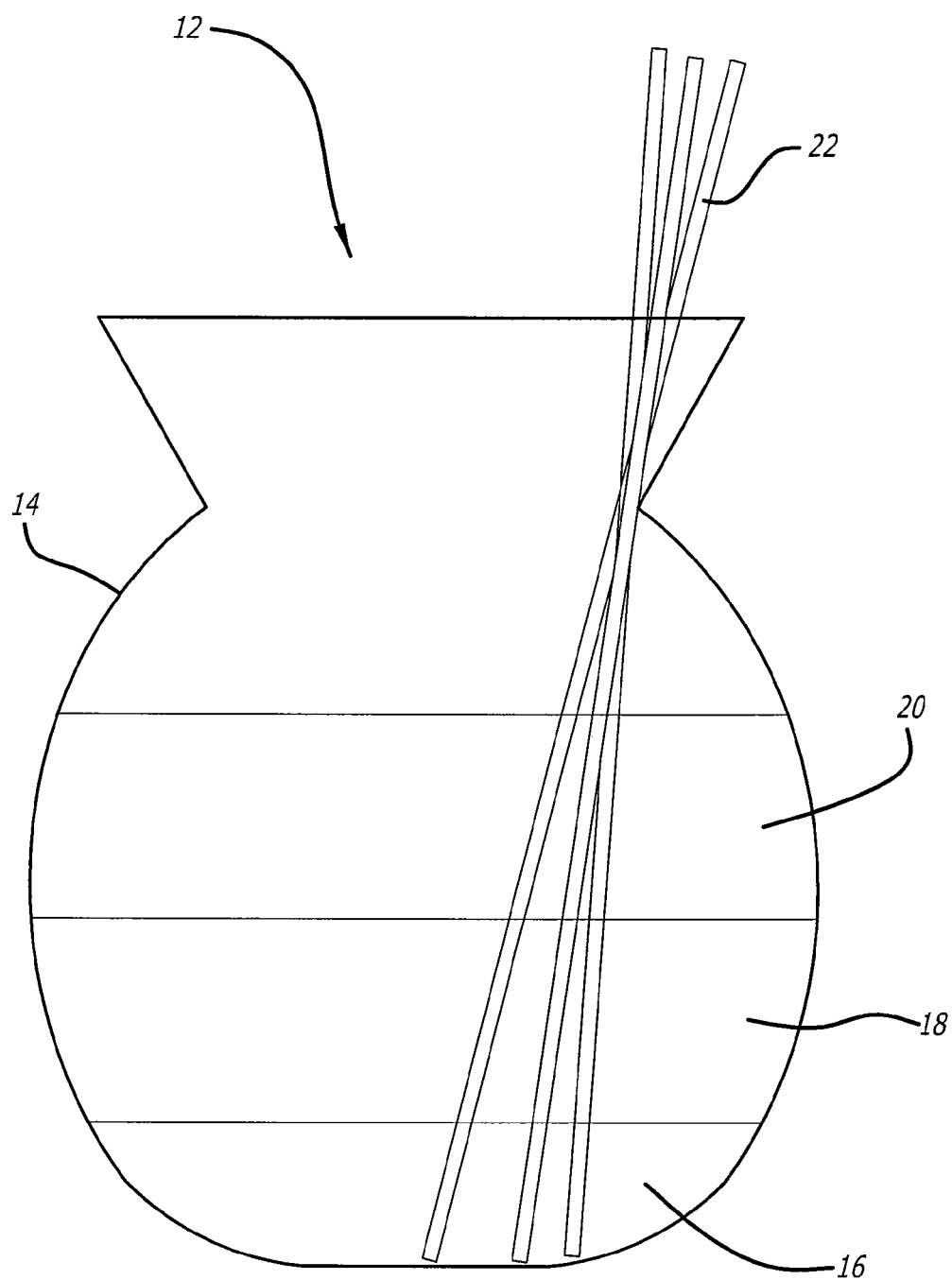
FIG. 1 is a representation of a preferred embodiment of the invention.

In accordance with the invention, a preferred embodiment of a three layer fragrance delivery system is formulated using a polar solvent (Class 1), a volatile silicone (Class 2) and an aryl alcohol (Class 3).

An aqueous component that will form one of the layers is first prepared by combining the following ingredients in the indicated amounts:

| AQUEOUS COMPONENT | |
| --- | --- |
| Ingredient | Weight in grams |
| Deionized water | 27.486 |
| Tetrasodium EDTA Dihydrate | 0.016 |
| Red 33 (25DA3733) Dye | 0.00039382 |
| Yellow 5 (21DA4400) Dye | 0.00026527 |
| | 27.503 |

The Tetrasodium EDTA Dihydrate serves as a chelating agent and a pH adjuster. Additional materials may be added including for example triethanolamine, citric acid, triethyl citrate, ethylenediamine tetra acetic acid and other salts thereof, sodium benzoate and phenoxyethanol/ethylhexylglycerin. To promote a more rapid and complete separation of layers, coalescing aids may also be added. For example, for water/oil, film formers such as isodecyl benzoate and 2,2,4-trimethyl-1,3-pentanediol monoisobutyrate may be used. For oil/oil, methyl phenyl silicone fluids may be incorporated.

A non-aqueous component that will ultimately form into two layers is prepared by combining the following ingredients in the indicated amounts:

| NON-AQUEOUS COMPONENTS | |
| --- | --- |
| Ingredient | Weight in grams |
| Dipropylene Glycol n-Propyl Ether (DPNP) | 14.946 |
| Decamethylcyclopentasiloxane (D5) | 32.500 |
| Benzyl Alcohol | 10.0 |
| Fragrance | 14.0 |
| 2,2,4-trimethyl-1,3-pentanediol monoisobutyrate | 0.9 |
| Red D858 Dye | 0.00059344 |
| Yellow D879 Dye | 0.000765 |
| Tinuvin 5060 | 0.15 |
| | 72.497 |

In addition to adjusting the specific gravity of the mixture, the Dipropylene Glycol n-Propyl Ether (DPNP) serves a controlling agent to the extent it maintains the Class 2 and Class 3 components in a single phase prior to mixing with the aqueous phase. Various glycol ethers and glycol ether esters may be used, preferably those that are derived by propoxylation of alcohols and in particular those derived from 2 or more moles of propylene oxide to 1 mole of an alcohol. Although Dipropylene Glycol Monomethyl Ether Acetate (DPMA) is a viable alternative, DPNP is preferred because of hydrolytic stability.

In the final step the aqueous components and the non-aqueous components are mixed with one another. The system will take 12-24 hours to separate into three layers and about another 24 hours (temperature and formulation dependent) may be needed in order to achieve total clarity in the middle layer. The non-aqueous components split into two layers as some of the water will dissolve in the non-aqueous mixture to promote the mutual immiscibility of the Class 2 (volatile silicone) and Class 3 (aryl alcohol) ingredients which the controlling solvent (DPNP) had been maintaining in a uniform phase. The resulting layered arrangement will be best suited for use with a moderately or relatively polar wicking material such as rattan. Accordingly, the top layer will be Class 2-rich and have specific gravity of 0.96 g/cm3, the intermediate layer will be Class 3-rich and have a specific gravity of 0.98 g/cm3 while the bottom layer will be Class 1-rich and have a specific gravity of 1.00 g/cm3. Ultimately, this system will result in a turquoise bottom layer, a purple intermediate layer and a pale violet top layer.

Insertion of a simple wick comprising a polar material, such one or more sticks of rattan, will allow the three liquids with the various materials dissolved therein to quickly and efficiently wick to the atmosphere. It is to be noted that although the deionized water, with a specific gravity of 1 g/ml, has a specific gravity intermediate the specific gravity of benzyl alcohol (1.045 g/ml) and that of D5 (0.956 g/ml), the addition of the various materials listed above renders the aqueous layer the most dense to therefore reside at the bottom of the three layers.

FIG. 1 is an illustration of a fragrance delivery system 12 of the present invention. A transparent or translucent container 14 is shown with the three discrete layers of liquid therein. An aqueous layer 16 resides at the bottom of the container below the aryl alcohol-rich layer 18 and a D5-rich layer 20. A plurality of simple wicks 22 serves to simultaneously deliver the three liquids to the atmosphere.

In an alternative preferred embodiment of the present invention, both a polar as well as a non-polar wick are relied upon enable the transfer of the liquids to the atmosphere. The use of a combination of rattan and fiber-glass wicks has been found to be especially effective.

While particular forms of the invention have been described and illustrated, it will also be apparent to those skilled in the art that various modifications can be made without departing from the spirit and scope of the invention. As an example, additionally or alternatively, other classes of materials may be used such as ionic fluids, mineral oils and hydroxy-functional fatty esters such as castor oil. Accordingly, it is not intended that the invention be limited except by the appended claims.

What is claimed is:

1. A fragrance delivery system, comprising:
   a first liquid;
   a second liquid, immiscible with said first liquid;
   a third liquid, immiscible with said first and second liquids
   a fragrance dissolved in one or more of said three liquids;
   a wick for simultaneously transporting said three liquids to an atmosphere.

2. The fragrance delivery system of claim 1, wherein said three liquids are contained in a transparent or translucent container.

3. The fragrance delivery system of claim 1, wherein said wick is formed of polar material and further comprising a second wick formed of non-polar material.

4. The fragrance delivery system of claim 3, wherein said polar material comprises rattan and said non-polar material is formed of fiber-glass.

5. A fragrance delivery system, comprising:
- a first liquid, wherein said first liquid has a first specific gravity;
- a second liquid, immiscible with said first liquid, wherein said second liquid has a second specific gravity wherein said second specific gravity is greater than said first specific gravity and wherein said second liquid is more polar than said first liquid;
- a third liquid, immiscible with said first and second liquids, wherein said third liquid has a third specific gravity wherein said third specific gravity is greater than said second specific gravity and wherein said third liquid is more polar than said second liquid;
- a fragrance dissolved in one or more of said three liquids; and a wick for simultaneously transporting said three liquids to an atmosphere, wherein said wick is formed of polar material.

6. The fragrance delivery system of claim 5, wherein said first liquid and second liquids comprise non-aqueous components and said third liquid comprises an aqueous component.

7. The fragrance delivery system of claim 6, wherein said second liquid comprises a aryl alcohol.

8. The fragrance delivery system of claim 5, wherein said second liquid comprises benzyl alcohol.

9. The fragrance delivery system of claim 6, wherein said first liquid comprises a volatile silicone.

10. The fragrance delivery system of claim 9, wherein said first liquid comprises decamethylcyclopentasiloxane.

11. The fragrance delivery system of claim 5, wherein said wicking material comprises rattan.

12. A fragrance delivery system, comprising:
- a first liquid, wherein said first liquid has a first vapor pressure and a first specific gravity;
- a second liquid, immiscible with said first liquid, wherein said second liquid has a second vapor pressure and a second specific gravity wherein said second vapor pressure is greater than said first vapor pressure and said second specific gravity is lower than said first specific gravity;
- a third liquid, immiscible with said first and second liquids, wherein said third liquid has a third vapor pressure and a third specific gravity wherein said third vapor pressure is greater than said second vapor pressure and said third specific gravity is lower than said second specific gravity;
- a fragrance dissolved in one or more of said three liquids; and
- a wick for simultaneously transporting said three liquids to an atmosphere, wherein said wick is formed of non-polar material.

13. The fragrance delivery system of claim 12, wherein said wicking material comprises non-woven fiberglass.

14. The fragrance delivery system of claim 12, further comprising a second wick formed of non-polar material.

* * * * *